United States Patent [19]

Rathbone

[11] 4,324,888

[45] Apr. 13, 1982

[54] PROCESS FOR THE PREPARATION OF CHLORODEOXYSUGARS

[75] Inventor: Elner B. Rathbone, Wokingham, England

[73] Assignee: Talres Development (N.A.) N.V., Curacao, Netherlands Antilles

[21] Appl. No.: 127,307

[22] Filed: Mar. 5, 1980

[30] Foreign Application Priority Data

Mar. 9, 1979 [GB] United Kingdom .............. 08392/79

[51] Int. Cl.$^3$ ............................................. C07H 5/02
[52] U.S. Cl. ..................................... 536/122; 536/119
[58] Field of Search .......................... 536/122, 4, 119

[56] References Cited

U.S. PATENT DOCUMENTS 4,117,224  9/1978  Khan et al. .................... 536/122

Primary Examiner—Blondel Hazel
Attorney, Agent, or Firm—Ostrolenk, Faber, Gerb & Soffen

[57] ABSTRACT

A process for the preparation of a chlorodeoxy derivative of a reducing aldose having a primary hydroxy group in an exocyclic -$CH_2OH$ group, in which the said primary hydroxy group is replaced by a chlorine atom to give a chlorodeoxy reducing sugar with a free anomeric center, characterized in that the free reducing sugar is reacted with a reagent comprising an N,N-dialkyl (methaniminium) chloride obtained by reacting an N,N-dialkyl formamide with a chlorinating agent.

7 Claims, No Drawings

PROCESS FOR THE PREPARATION OF CHLORODEOXYSUGARS

The present invention relates to chlorodeoxysugars, and in particular to a process for selectively replacing one particular hydroxy group of a reducing aldose sugar, for example, glucose, with a chlorine substituent.

In common with other reducing sugars, glucose exists in solution as an internal, cyclic hemi-acetal with a free anomeric centre. For D-glucose, one form of hemi-acetal is known as D-glucopyranose, reflecting the notional derivative from pyran.

D-glucose in its pyranose ring form has one primary and four secondary hydroxy groups which could be replaced singly or plurally by chlorine substituents.

The chlorodeoxysugars are of interest for various reasons. In particular, it has been discovered that 6-chloro-6-deoxy derivatives of certain sugars possess spermicidal activity. As is discussed in British pending application No. 10694/77 (which corresponds to published Belgian Pat. No. 864859), these chlorinated sugars are therefore of interest as antifertility agents.

The present invention is concerned with the synthesis of the potentially important 6-chloro-6-deoxy derivatives of reducing sugars.

As mentioned above, D-glucopyranose has five hydroxy groups which can be replaced by chlorine substituents, and there are thus five possible monochlorinated derivatives. However, the hemi-acetal linkage of a reducing sugar is particularly labile, and it is usually the case that any reaction of glucose or other reducing sugar occurs first at the anomeric centre. Thus, for example, D-glucopyranose is oxidised by bromine-water at $C_1$ to give the corresponding gluconolactone.

For the synthesis of a chlorodeoxy derivative of a reducing sugar, other than a $C_1$ chlorinated sugar, it has therefore been considered essential to protect the anomeric centre. Typically the centre has been protected by initial reaction of the sugar with an alcohol to form the full acetal or glycoside. The reactivity at the anomeric centre is such that the corresponding alkyl glycoside is readily formed by reaction of a sugar with an alcohol. Thus, the conventional starting material for chlorination reactions has always been a glycoside or other protected derivative rather than the free sugar.

It is known that the primary hydroxy group of certain methyl glycosides, e.g. the 6-hydroxy substituent of a hexopyranoside, can be selectively replaced with a chlorine atom by using methanesulphonyl chloride in N,N-dimethylformamide. For example, Evans, Long and Parrish have used this reagent to prepare the 6-chloro-6-deoxy derivatives of methyl β-D-glucopyranoside and methyl α-D-mannopyranoside (J. Org. Chem., 37,1074 (1968)). However, in using this reagent, it has always been the practice to use a glycoside, and not the free sugar. When other halogenating agents are employed with alkyl glycosides, it is usually the case that other chlorinated products are obtained. For example, sulphuryl chloride gives principally a mixture of dichloro-dideoxy derivatives with methyl α-D-glucopyranoside (Carbohyd. Res., 33, 383 (1974)).

As an example of the reaction of a halogenating agent with a free reducing sugar, the reaction of sulphuryl chloride with glucose itself is typical: it was found that syrupy products were obtained (Can. J. Chem., 40, 1408 (1962)). Further investigation of the products not surprisingly gave evidence that the glucose had reacted at the anomeric centre; the initial syrup was presumed to contain a compound corresponding to chlorination at the 1-, 4- and 6-positions. Similar results were obtained with xylose and maltose.

In contradistinction to the teachings of the prior art, we have now found that the primary hydroxy group in the exocyclic $-CH_2OH$ grouping of a reducing aldose, e.g. the 6-hydroxy group of glucose, can be chlorinated by direct reaction of a specified halogenating agent with the free sugar, without the need for protecting the anomeric centre.

In accordance with the present invention, there is provided a process for the preparation of a chlorodeoxy derivative of a reducing aldose, having a primary hydroxy group in an exocyclic $-CH_2OH$ group, in which the said primary hydroxy group is replaced by a chlorine atom to give a chlorodeoxy reducing sugar with a free anomeric centre, characterised in that the free reducing sugar is reacted with a reagent comprising an N,N-dialkyl (methaniminium) chloride.

The N,N-dialkyl (methaniminium) halide derivatives are a class of halogenating reagents described by, inter alia, Haines in a review article in Advances in Carbohydrate Chemistry and Biochemistry in 1976 (pages 80–83). A dialkylformamide reacts with various chlorinating agents to form a reactive intermediate which is believed to be an N,N-dialkyl(methaniminium) chloride. The chlorinating agent may, for example, be selected from hydrocarbon sulphonyl chlorides, phosgene and thionyl chloride. Particularly preferred are the hydrocarbon sulphonyl chlorides, e.g. those in which the hydrocarbon group is an alkyl or alkaryl group, such as methanesulphonyl chloride and p-toluenesulphonyl chloride. Thus, N,N-dimethyl-formamide and methanesulphonyl chloride yield the compound

$$[XYC=N^{30}(CH_3)_2] \ Z^- \qquad (I)$$

where X represents a methanesulphonyloxy group; Y represents a hydrogen atom and Z represents a chlorine atom. Other halogenating agents give different compounds of formula (I). For example, DMF with p-toluenesulphonyl chloride gives compound of formula (I) in which X represents a p-toluenesulphonyloxy group, while phosgene or thionyl chloride give initially compounds in which X represents a chloroformate or chlorosulphate group, respectively, both decomposing to give finally a compound in which X represents a chlorine atom.

It will be appreciated that this formula is perhaps only hypothetical and the scope of the present invention is not bound by theory. The chlorinating agent to be used is thus one which is of the type believed to comprise an N,N-dialkyl(methaniminium) chloride, e.g. a compound of the formula (I) as defined above.

The chlorinating intermediate is formed by contacting one of the chlorinating agents mentioned above with an N,N-dialkylformamide such as DMF or diethylformamide. Equivalent formyl derivatives may also be suitable, for example, a cyclic derivative such as N-formylpiperidine.

It is believed that the cation of such a compound is sterically hindered from attacking glucose at the 4-position, and that whereas sulphuryl chloride chlorinated glucose at the 1,4 and 6 positions (see Can. J. Chem., op. cit.), the cation initially chlorinates at only the 1 and 6 positions. Thereafter, work-up of the crude product gives the desired 6-chloro-6-deoxy glucose, apparently by virtue of non-destructive hydrolysis at the 1-position.

The present reaction is preferably performed by dissolving the reducing sugar in the solvent, i.e. the formamide, adding the chlorinating agent to form a chlorinating intermediate, effecting chlorination, and working up the initial product in a manner which includes a mild hydrolysis.

The conditions under which the chlorination reaction is effected will depend, of course, on the nature of chlorinating reagent used.

Where methanlsulphonyl chloride and DMF are reacted to form the reagent, a typical procedure is to dissolve the sugar in the formamide solvent, if necessary with heating, cool the solution and add the chlorinating agent, heat the reaction mixture to effect chlorination e.g. for 2 to 50 h at 20° to 90° C., and then heat the initial product with water e.g. for 1.5 to 10 hours at 40° to 100° C., and thereafter isolate the chlorodeoxy sugar. A preferred ratio of chlorinating agent (i.e. the reagent added to the formyl compound) to reducing sugar is in the range 4 to 10 equivalents to 1 equivalent. The chlorodeoxy compound can be purified, e.g. by formation and crystallisation of a per-esterified derivative, followed by de-esterification. The acetyl ester is preferred.

Where a chlorinating agent other than a hydrocarbonsulphonyl chloride is reacted with DMF, for example, reaction of thionyl chloride with DMF, the conditions for the chlorination of the sugar may need to be much milder. Thus, for example, the reaction with the sugar may be effected at a very low temperature, e.g. at or below 0°.

As explained above, the sugar itself maybe any reducing aldose possessing an exocyclic —CH$_2$OH group. The monosaccharide hexoses of this type give 6-chloro-6-deoxy derivatives which exhibit male anti-fertility activity. Disaccharides such as maltose may be chlorinated to give "dimers" of such 6-chloro-monosaccharides, which can be hydrolysed to yield the free 6-chloro-monosaccharide(s). Thus, for example, maltose can be chlorinated according to the present invention to give 6,6'-dichloro-6,6'-dideoxymaltose, which can be hydrolysed to produce two molecules of 6-chloro-6-deoxy glucose.

The present invention is illustrated by way of the following non-limiting examples.

EXAMPLE 1

6-Chloro-6-deoxy-D-glucose

D-Glucose (10 g) was dissolved in DMF (100 ml) with warming. The solution was cooled to 0° C. and methanesulphonyl chloride (47 ml) was added dropwise with stirring. The solution was stirred at 60° on an oil bath for 24 hours in a stoppered flask. Water (100 ml) was added and heating continued for 2 hours. The mixture was filtered, the filtrate extracted with dichloromethane (2×200 ml) and the aqueous solution evaporated to dryness; traces of DMF were co-distilled off with toluene using first a water pump, followed by an oil pump.

To effect purification, the residue was dissolved in pyridine (100 ml), the solution cooled to 0° C., and acetic anhydride (60 ml) added. The solution was left at room temperature for 18 hours, heated to 50° C. for 1 hour, poured into ice-water (300 ml) and stirred for 1 hour. The mixture was extracted with dichloromethane (3×300 ml) and the organic layer washed sequentially with cold 10% sulphuric acid (2×100 ml), sodium bicarbonate solution (2×100 ml) and water (2×100 ml). The solution was dried over sodium sulphate, filtered and evaporated to a residue which solidified on addition of ethanol. The solid was dissolved in hot ethanol, decolorised with charcoal, and allowed to crystallise. The product was filtered off and dried overnight under vacuum. Yield 14 g. (68%) of 6-chloro-6-deoxy-glucose tetraacetate.

The dry acetate is dissolved in methanol (30 ml) and sodium methoxide (1 ml of a 1 M solution in methanol) is added to the cooled (0° C.) solution. The solution is kept at 0° overnight, Zerolit DMF mixed ion-exchange resin (H$^+$/CO$_3^{2-}$) is added, the mixture filtered, and the filtrate evaporated to a residue. The residue is dissolved in 50% ethanol, decolourised on charcoal, evaporated to dryness, and the residue crystallised and recrystallised from ethanol-ether. The product is dried overnight under vacuum to yield 6.3 g (57% overall) of 6-chloro-6-deoxy-D-glucose which gave the same i.r. and n.m.r. spectra as an authentic sample (Evans et al op. cit.; obtained in approximately 35% yield from glucose via the glucoside).

EXAMPLE 2

6-Chloro-6-deoxy-D-mannose

The technique of Example 1 was repeated, but using mannose (10 g) in place of D-glucose. There was obtained 6-chloro-6-deoxy-mannose (3.9 g; 35% overall) which was identical to a sample produced from methyl D-mannopyranoside.

EXAMPLE 3

6,6'-Dichloro-6,6'-dideoxy-maltose

Maltose (2.2 g) was dissolved in DMF (25 ml) and treated with mesyl chloride (10 ml) as described in Example 1. After being heated at 60° for 20 h, the reaction was cooled, water was (25 ml) added and the mixture was heated at 60° for 2 h. The product was recovered and acetylated (Example 1). The acetylation mixture was poured into ice/water (250 ml) and stirred, whereupon a precipitate formed. The solid was filtered off, decolourised (charcoal) and recrystallised from ethanol; yield 2.64 g. The product was identified as 6,6'-dichloro-6,6'-dideoxymaltose hexaacetate: t.l.c. R$_F$0.31 (silica gel; petroleum ether-ethyl acetate, 1:1); m.p. 187°–188° C.; [α]$_D^{20}$+38° (c 1.0, chloroform); mass spectrum, m/e 307, 247, 205 and 187; n.m.r.

| | |
|---|---|
| 4.23 | (doublet, 1 proton H-1, J 1,2 7.6 Hz), |
| 5.01 | (triplet, 1 proton H-2, J 2,3 7.6 Hz), |
| 4.67 | (triplet, 1 proton H-3, J 3,4 4.67 Hz) |
| 5.76 | (triplet, 1 proton H-4, J 4,5 7.6 Hz), |
| 6.07 | (multiplet, 3 protons H-5, 6a, 6b,), |
| 4.48 | (double, 1 proton H-1' J 1', 2' 3.6 Hz), |
| 5.15 | (quartet, 1 proton H-2' J 2', 3' 9.6 Hz), |
| 4.61 | (triplet, 1 proton H-3' J 3', 4' 9.2 Hz), |
| 4.88 | (triplet, 1 proton H-4' J 4', 5' 9.2 Hz), |
| 5.91 | (sextet 1 proton H-5' J 5', 6a' 4.0 Hz) and J 5', 6b' 3.2 Hz), |
| 6.24 | (quartet, 1 proton H-6a' J 6a', 6b' −12.0 Hz), |
| 6.39 | (quartet, 1 proton H-6b'), |
| 7.89 | (singlet, 3 protons acetate), |
| 7.95 | (singlet, 3 protons acetate), |
| 7.96 | (singlet, 6 protons 2 × acetate), and |
| 7.99 | (singlet, 6 protons 2 × acetate). |

The hexaacetate was dissolved in methanol (5 ml) and deacetylated (01. ml of 1 M sodium methoxide in methanol) to give 6,6'-dichloro-6,6'-dideoxymaltose (P. Colson, K. N. Slessor, H. J. Jennings and I. C. P. Smith, Can. J. Chem., 53, 1030, 1975) as a syrup; yield 0.9 g (85% from hexaacetate); $[\alpha]_D^{20} + 95°$ (c 1.0, water).

EXAMPLE 4

6-Chloro-6-deoxyglucose

The syrup from Example 3 (0.9 g) was dissolved in 0.5 N hydrochloric acid and Amberlyst 15 (H+) resin (1 g) was added. The mixture was heated at 90° until t.l.c. (dichloromethanol-methanol, 4:1) showed complete hydrolysis to a faster-moving product (about 2 h). The mixture was filtered, neutralised (Zerolit DMF, $H^+/CO_3^{2-}$) and evaporated to a syrup which crystallised on addition of ether-ethanol (9:1) and seeding with a small amount of 6-chloro-6-deoxy-D-glucose. The product (0.7 g; 32% overall) was recrystallised from ethyl ether-ethanol and shown to be identical to an authentic sample of 6-chloro-6-deoxy-D-glucose.

I claim:

1. A process for the preparation of a chlorodeoxy derivative of a reducing aldose having a primary hydroxy group in an exocyclic —CH$_2$OH group, in which the said primary hydroxy group is replaced by a chlorine atom to give a chlorodeoxy reducing sugar with a free anomeric centre, characterised in that the free reducing sugar is reacted with a reagent comprising an N,N-dialkyl (methaniminium) chloride obtained by reacting an N,N-dialkyl formamide with a chlorinating agent and such chlorination is followed by a mild hydrolytic work up.

2. A process according to claim 1, in which the said chlorinating agent is selected from hydrocarbonsulphonyl chlorides, phosgene and thionyl chloride.

3. A process according to claim 2, in which the said chlorinating reagent is an alkanesulphonyl or alkaranesulphonyl chloride.

4. A process according to claim 1, in which the N,N-dialkyl formamide is N,N-dimethyl formamide or N,N-diethyl formamide.

5. A process according to claim 1 in which the ratio of the chlorinating agent to reducing sugar is in the range 4–10 equivalents to 1 equivalent.

6. A process according to claim 1 in which the product is purified by the formation of a per-esterified derivative which is subsequently de-esterified.

7. A process according to claim 3, in which the chlorination is effected at an elevated temperature.

* * * * *